United States Patent [19]

Rhoades et al.

[11] Patent Number: 4,587,479
[45] Date of Patent: May 6, 1986

[54] CORROSION MEASUREMENT WITH MULTIPLE COMPENSATION

[75] Inventors: Rex V. Rhoades, Anaheim; Charles M. Finley, Arcadia, both of Calif.

[73] Assignee: Rohrback Corporation, Seattle, Wash.

[21] Appl. No.: 631,197

[22] Filed: Jul. 16, 1984

[51] Int. Cl.⁴ ........................................ G01R 27/02
[52] U.S. Cl. ............................ 324/65 CR; 324/71.2
[58] Field of Search ............ 324/71.2, 65 CR, 65 CP, 324/65 R

[56] References Cited

U.S. PATENT DOCUMENTS

| | | | |
|---|---|---|---|
| 2,735,754 | 2/1956 | Dravnieks | 324/65 CR |
| 2,993,366 | 7/1961 | Birkness | 73/86 |
| 3,067,386 | 12/1962 | Freedman | 324/65 CR |
| 3,073,154 | 1/1963 | Schaschl et al. | 73/86 |
| 3,104,355 | 9/1963 | Holmes et al. | 324/71 |
| 3,936,737 | 2/1976 | Jefferies, Sr. | 324/65 |
| 4,019,133 | 4/1977 | Manley et al. | 324/65 |
| 4,160,948 | 7/1979 | Tytgat et al. | 324/61 |
| 4,217,544 | 8/1980 | Schmidt | 324/65 |
| 4,262,247 | 4/1981 | Olson et al. | 324/65 |
| 4,266,188 | 4/1981 | Thompson | 324/65 R |
| 4,326,164 | 4/1982 | Victor | 324/71 |
| 4,338,563 | 7/1982 | Rhoades et al. | 324/65 |
| 4,398,145 | 8/1983 | Quayle | 324/62 |
| 4,412,174 | 10/1983 | Conlon | 324/65 CR |

Primary Examiner—Reinhard J. Eisenzopf
Assistant Examiner—Jose M. Solis
Attorney, Agent, or Firm—Gausewitz, Carr and Rothenberg

[57] ABSTRACT

An electrical resistance-type corrosion measuring probe provides an output signal corrected for temperature by computing the ratio of resistance of a test element exposed to a corrosive element to resistance of a reference element protected from the environment. A secondary temperature compensation is provided for by compensating the corrosion output signal for dynamic or short term variation of temperature difference between test and reference elements. The corrosion output signal is compensated for still other environmentally induced errors by measuring temperature gradient between an inner end of the probe within the fluid environment and a portion of the probe outside the corrosive fluid environment. Errors in corrosion probe output signal due to bending stresses on the probe that result from fluid flow velocity and fluid pressure of the environment, are also compensated by measuring bending strain and pressure to provide additional compensation for the corrosion output signal.

33 Claims, 6 Drawing Figures

CORROSION MEASUREMENT WITH MULTIPLE COMPENSATION

BACKGROUND OF THE INVENTION

This invention relates to measurement of corrosive characteristics of a fluid and more specifically concerns improved compensation for errors in such measurement that are due to one or more of several different environmental variables.

A common method of measurement of corrosion characteristics of a corrosive environment, such as a liquid or gas confined in a pipe or other vessel, employs resistance measurement of a metallic corrodible test element to indicate, by change in electrical resistance, the amount of metal that has been lost by corrosion over a period of time. The term corrosion, as employed in this description, also covers erosion, a process that is also measured by electrical resistance methods such as illustrated in U.S. Pat. No. 3,104,355 to Holmes et al. A widely used device for measurements of this type is known as a Corrosometer probe manufactured by Rohrback Corporation, assignee of this application. In a probe of this type, a sacrificial electrical resistance element is inserted into a corrosive environment. The probe also carries a reference element made of the same material as the test element. Alternating current is passed through the elements and electrical resistance of each is measured while and after the probe has been immersed in an environment of which corrosive tendencies are to be monitored. Because the resistance of the test element changes with the amount of metal of the element, measurement of resistance changes provides an indication of corrosion. However, because resistance of the metal also changes with temperature, a reference element is provided, made of the same material as the test element and having the same temperature resistance characteristics. Changes in resistance of the test element that are due to long-term, relatively slow temperature variation, are eliminated by comparison of resistances of the test and reference element. Commonly, the ratio of resistance of test element to resistance of reference element is measured by means of a Wheatstone bridge or equivalent.

In U.S. Pat. No. 4,338,563 for Corrosion Measurement with Secondary Temperature Compensation, there is described a method of compensating for dynamic or short-term variation of temperature of the environment by directly measuring temperature of both test and reference elements and compensating the corrosion signal according to the directly measured short-term temperature difference of the elements.

Corrosion measurements made with electrical resistance instruments, even with the secondary compensation of U.S. Pat. No. 4,338,563, are widely useful for measurement of relatively long-term (weeks or months) corrosion rates, but provide little or no useful accurate information with respect to relatively slight amounts of metal depletion that occurs in shorter periods of time such as hours or days. Metal losses for many systems are in the order of millionths of an inch per hour, with concomitant test element resistance changes in tenths of a micro-ohm. Measurement of such low level changes for accurately determining small amounts of corrosion are exceedingly difficult, if not impossible, because of the amount of unwanted noise in the desired corrosion signal. Such noise includes both correlated noise (variations of the corrosion output signal that are some function of a variable of the environment being monitored) and uncorrelated noise (variations of output signal not related to environment variables). The environmental variables that cause correlated noise actually cause changes in the resistance of the test or reference elements to thereby falsely signal a different rate of corrosion.

U.S. Pat. No. 4,338,563, to Rhoades et al., and U.S. Pat. No. 4,217,544, to Schmidt, provide compensation for temperature induced errors by measuring both or one of test and reference element temperatures at selected points. However, since there is a continuous temperature gradient along the probe between the inner end of the probe, at or within the corrosive environment, and the outer end of the probe, outside of the environment, temperature measurement at a selected point on one or both elements does not adequately compensate for output signal error due to temperature induced noise.

There exist other sources of correlated noise, that is, signal errors caused by other environmental variables, which errors have not heretofore been eliminated. These additional sources of correlated noise include strain on the test element resulting from bending experienced by relatively long, narrow test elements, and induced by fluid flow velocities, and strain on the thin plate or membrane type test element of a flush probe that is subject to variation of fluid pressure.

Accordingly, it is an object of the present invention to provide corrosion measurement of increased precision.

SUMMARY OF THE INVENTION

In carrying out principles of the present invention, in accordance with a preferred embodiment thereof, an electrical resistance-type corrosion probe that provides a corrosion signal representing corrosion of a test element and compensated for temperature of the environment, is further compensated for fluctuation of environmental variables that affect the corrosion signal. Variables employed to compensate the corrosion signal include one or more of (a) the temperature gradient, such as gradients along the probe element, between the environment and a point adjacent the probe outside the environment, (b) the velocity of fluid flowing in the environment, which creates strain on the electrical resistance test element, (c) pressure of fluid of the environment, which also creates strain on the test element, and (d) other, similar variables which can affect the value of the corrosion measurement, and which may be measured by independent means. Such compensations diminish errors of the output signal caused by fluctuation of environment variables. These variables actually cause changes in resistance of the test element, which changes are not due to the corrosion that is to be measured. According to another feature of the invention, improved means are provided for more accurately and precisely combining a compensation factor with the corrosion signal.

The output signal of a corrosion instrument includes other errors due to uncorrelated noise. Examples of such noise include effects of powerline pickup, line voltage variations, electromagnetic pickup, thermoelectric voltages, internally generated amplifier noise and amplifier input and gain variations. Effects of such noise are diminished by periodically sampling the test and reference electrical resistance signals, averaging the sampled values over a selected period of time, and employing the averaged values for ratio computation.

DETAILED DESCRIPTION

Figure 1:
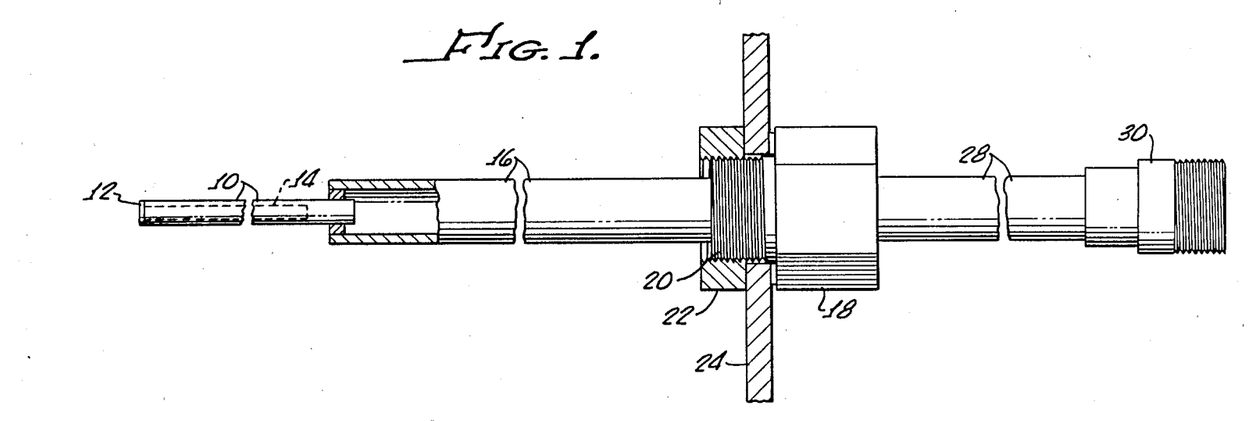
FIG. 1 illustrates a typical tubular electrical resistance probe and a fragment of a wall of a vessel in which the probe is mounted.

Illustrated in FIG. 1 is a tubular corrosion probe of a type known as a Corrosometer probe manufactured by Rohrback Corporation. In this probe, the test element is a thin outer shell 10, having its outer end closed by a fixedly secured disc 12, to which is also secured an inner or reference element 14 formed from the same material as the outer shell, which may be a mild steel, for example. The two elements are electrically and physically connected by the disc 12 and the shell is filled with an electrically insulative but thermally conductive potting compound such as Sauereisen cement. This compound, though thermally conductive, has far less thermal conductivity than the metal of the test and reference elements.

The tubular assembly of test and reference elements is fixedly mounted to and partially within a probe body 16, having a fitting including a tool receiving head 18 and a threaded neck 20 that is adapted to be threadedly received within a suitable female threaded fitting 22 formed in a wall 24 of a pipe or other vessel that confines a corrosive fluid of which corrosive tendencies are to be measured. The probe body has a fixed tubular connector section 28 terminating in a probe electrical connector 30 in which terminate the several wires, to be described below, that are connected to the probe elements and extend through the tubular probe assembly and probe body for connection to a cable, not shown in FIG. 1, that leads to electrical circuitry to be described below.

Figure 2:
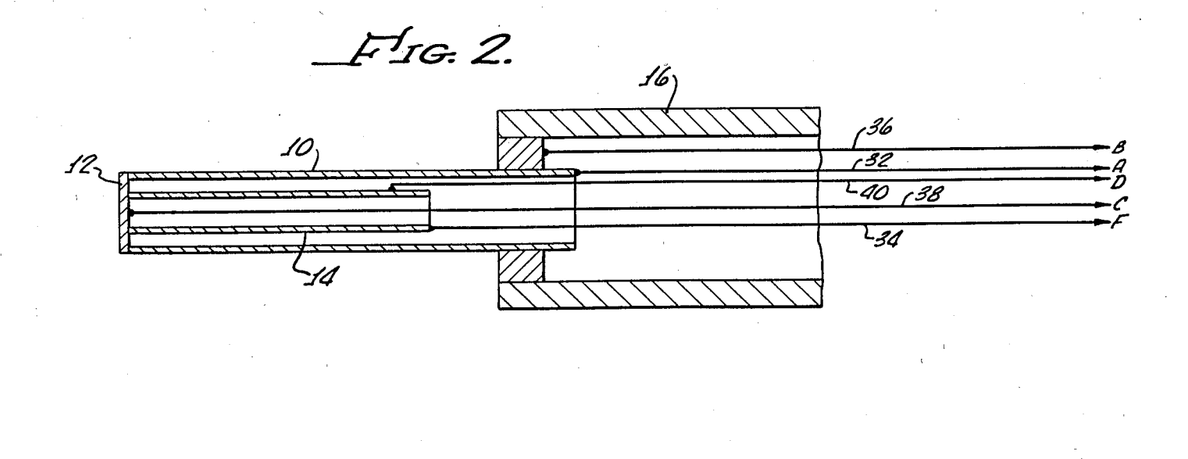
FIG. 2 is a schematic illustration of the probe of FIG. 1 and its electrical connecting leads.

Schematically illustrated in FIG. 2 are portions of the probe assembly of FIG. 1 showing the several electrical leads, all (except two described more particularly below) being made of a conventional conductive material of the type commonly employed in instruments of this type. Leads 32 and 34 are connected to ends of the test and reference elements, respectively, and extend to terminals A and F of the probe connector 30 where they are connected via a cable, not shown, to a source of AC current. This AC current is supplied through electrical leads 32, 34, flowing through the test element 10, through the electrically conductive header disc 12, and through the reference element 14. Electrical resistance of the test element is measured via leads 36 and 38 connected respectively to the probe body 16 adjacent the inner end of test element 10, and to the inner surface of the end closure disc or header 12, and terminating at connector terminals B and C, respectively. Electrical resistance of reference element 14 is measured via leads 38 and 40, lead 40 being connected to the reference element near its inner end and to probe connector terminal D.

Resistance of the test element between terminals B and C and resistance of the reference element between terminals D and C are compared to provide a corrosion measurement signal. Leads 38 and 40 are made of thermocouple wire, such as Constantan, for example, to provide a DC voltage between terminals C and D that is directly proportional to the differential temperature between the points on the test and reference elements to which these leads are connected. These leads are used for secondary temperature correction in a manner generally as described in U.S. Pat. No. 4,338,563 to Rhoades, et al., but with certain important improvements, as described below.

The tubular probe illustrated in FIGS. 1 and 2 is typical of several different types of probes having a test element that extends in a cantilevered fashion from the probe body and from the inner wall of the vessel, to project into the corrosive fluid of the environment. Such relatively long and slender probes include (in addition to the illustrated tubular probe) loop probes, wherein a loop of test element extends outwardly from the probe body into the environment and includes a return section extending back into the probe body. Such loop probes may be made of a tubular material, a ribbon-type material having a rectangular cross section, or a circular section wire.

Figure 3:
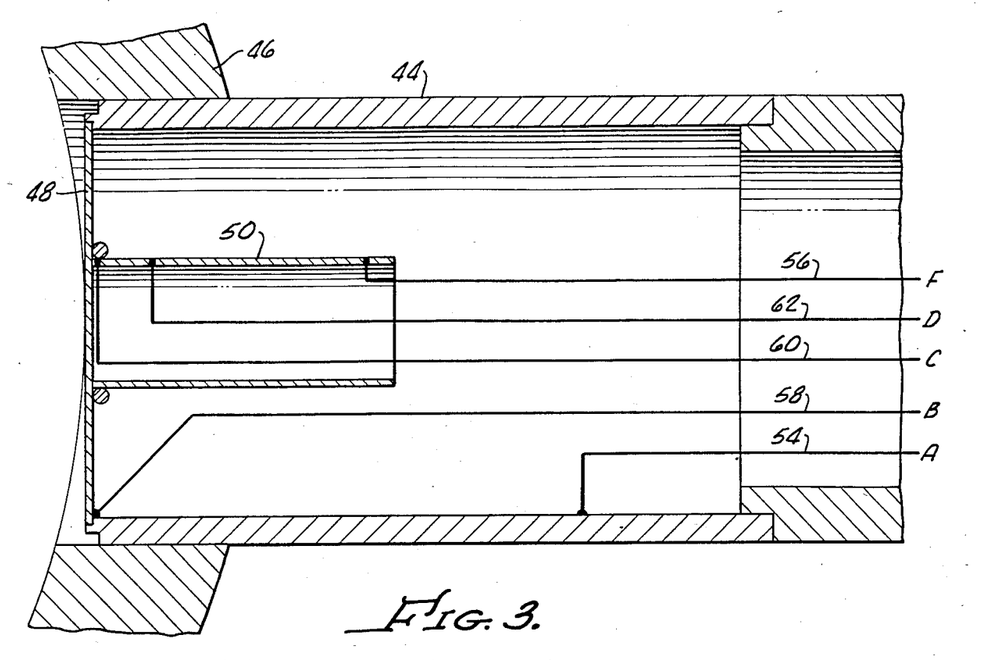
FIG. 3 illustrates an end portion of an exemplary flush probe.

A flush-type electrical resistance probe is shown in the fragmentary illustration of FIG. 3 wherein a probe body 44 is securely mounted in a wall 46 of a pipe or other vessel confining a corrosive fluid, and has its inner open end closed by a thin membrane like disc 48 that forms the corrosion test element. A tubular reference element 50, made of the same material as test element disc 48, may be formed integrally with the test element or otherwise secured to the inner surface of the disc element, with the space between the probe body, test and reference elements filled by a suitable electrically insulative and thermally conductive material. In the flush probe, power leads 54 and 56 are brought into the probe from terminals A and F to be connected to the probe body and to the inner end of the reference element, respectively. Resistance of the test element is measured at terminals B and C connected by leads 58, 60 to the outer and inner portions of the test disc 48. Resistance of the reference element is measured at terminals C and D, of which terminal D is connected by a lead 62 to an inner portion of the reference element 50. If secondary temperature compensation is employed in the flush probe of FIG. 3, leads 60 and 62 may be made of thermocouple wire to provide a direct reading at terminals C and D of the difference in temperature between the reference and test elements.

The thin membrane like test element 48 of the flush probe of FIG. 3 is subject to relatively little strain due to flow velocity (when flow is parallel to the test element surface), but is significantly more sensitive to pressure of the fluid within the environment. Pressure tends to bend the thin disc 48, which is supported primarily at its periphery and less rigidly by the material that fills the probe body.

A long, slender probe, such as the tubular probe illustrated in FIG. 1 and comparable loop-type probes, are more sensitive to strain due to fluid flow velocity. Those probes having a loop element formed of a solid rectangular or circular section ribbon or wire, are relatively insensitive to strain due to fluid environment pressure, whereas a loop test element of tubular cross section may be more sensitive to strain due to both fluid flow velocity and fluid pressure.

Figure 4:
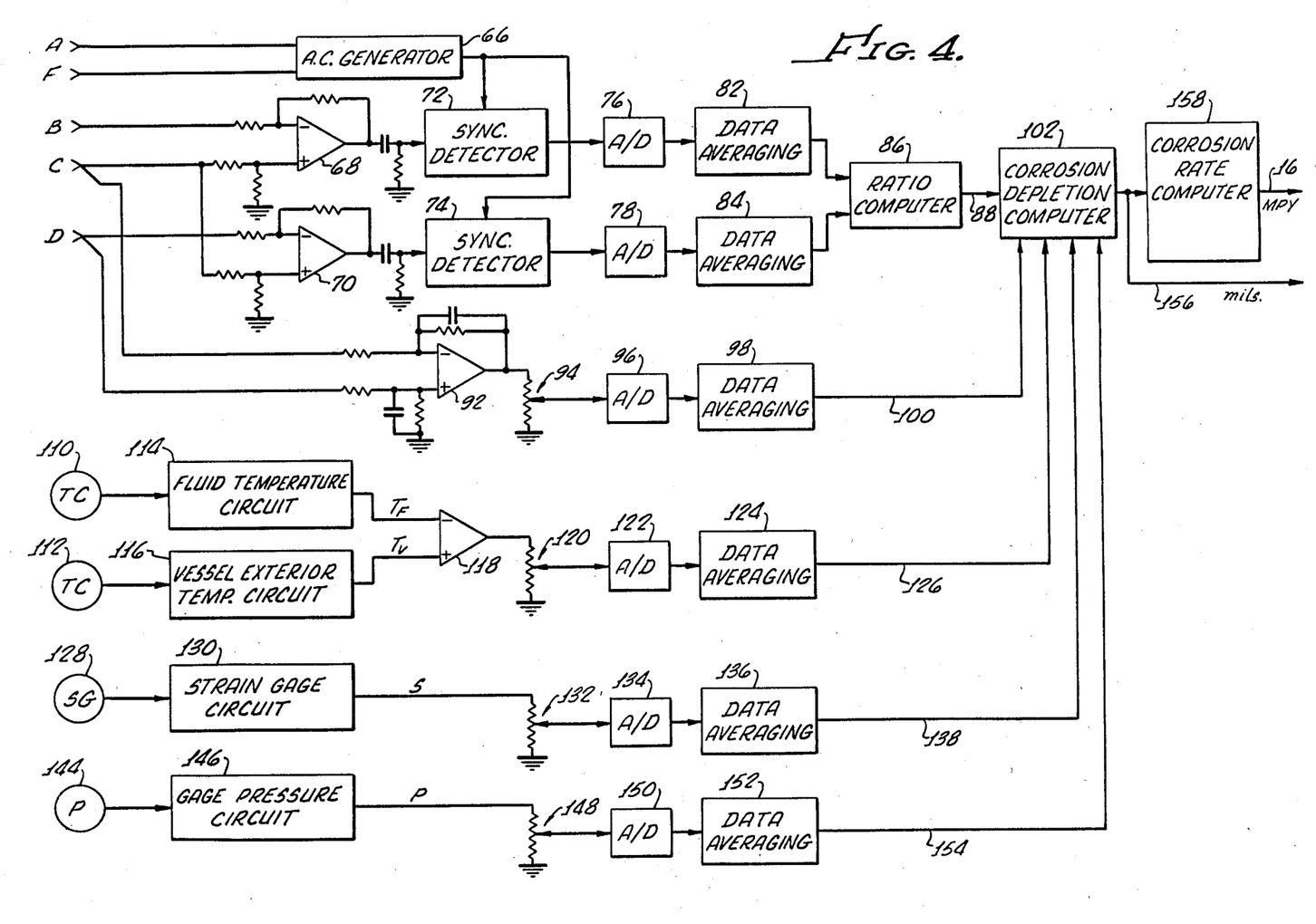
FIG. 4 illustrates an electrical circuit for providing compensation for several different environment varibles.

As illustrated in FIG. 4, AC power source 66, which may be a constant current AC generator, or a varible current source where current level is adjusted to maintain a constant voltage across the reference element, is connected to terminals A and F to provide, preferably, a balanced square wave, although a sine wave or modified square wave may also be employed. Signals from probe terminals B and C are fed to inverting and noninverting inputs of an AC coupled differential amplifier 68, and the signals from terminals C and D are fed to the noninverting and inverting inputs of a second AC coupled differential amplifier 70 that is matched with and is nearly identical in gain with amplifier 68. The AC voltage signals at the outputs of amplifiers 68 and 70 are fed to respective synchronous detectors 72, 74, each of which is referenced from the power source 66, and each of which provides as its output an analog signal representative of measured resistance. These analog resistance signals are fed to respective analog-to-digital converters 76, 78 to provide digital signals that are fed to respective digital averaging circuits 82, 84. Each averaging circuit periodically (at periods of several milliseconds) samples its input digital signal and stores the samples for a period of time. At the end of each storage period (in the order of seconds), all stored signals are averaged to provide an averaged digital output that is fed from each of the averaging circuits to a ratio computer 86. For each averaging period the computer repetitively computes the ratio of test resistance to reference resistance, thereby to provide a corrosion output signal on an output line 88.

The analog inputs to converters 76, 78 are subject to both correlated and uncorrelated noise. After conversion to digital form, additional electrical noise and effects of the environment are of no serious consequence. The averaging of the digital resistance signals diminishes unwanted and uncorrelated signal noise, including effects of powerline pickup, line voltage variations, electromagnetic pickup, thermal electric voltages, internal amplifier noise, amplifier gain, and input drift.

Secondary temperature compensation, for purposes described in U.S. Pat. No. 4,338,563, is provided by feeding the two thermocouple measured temperature signals at terminals C and D to the inverting and noninverting inputs of a DC coupled differential amplifier 92 of which the output is fed to a sensitivity adjusting potentiometer 94. The signal from the adjusting potentiometer 94 is fed to an analog-to-digital converter 96, which in turn feeds to a digital averaging circuit 98 similar in operation to circuits 82 and 84. The averaging circuit provides on its output line 100 a digital signal comprising the secondary temperature compensation signal as averaged over the averaging period of circuit 98. The secondary temperature compensation signal on line 100 is combined with the corrosion output signal on line 88 in a corrosion depletion computing circuit 102. This circuit does not merely algebraically combine the measured temperature difference with the measured resistance ratio, as in U.S. Pat. No. 4,338,563. Rather, it computes a compensation factor which is divided by the measured resistance ratio to provide a corrected resistance ratio according to a system equation (set forth below) that defines system operation.

As an example of the computation carried out by the circuit 102, consider a new tubular probe made of iron, having a 20 mil test element wall thickness. Assuming the time averaged resistance of each of the test and reference elements is one milli-ohm at a temperature of 20° centigrade, the ratio of test element resistance to reference element resistance, at the output of the ratio computer 86, is 1.000. Because the temperature coefficient of resistance of iron is commonly taken to be 0.0065 milli-ohm per milli-ohm per degree centigrade, if the temperature of both elements rises to 21° centigrade, the resistance of each element would be 1.0065 milli-ohms. The ratio computer would again provide an output of 1.000 because for primary temperature compensation. The measured test element resistance is divided by the measured reference element resistance to get the desired ratio. However, if the reference and test elements are not at the same temperature, so that the test element, for example, is at 21° centigrade whereas the effective temperature of the reference element remains at 20° centigrade, the resistance ratio would be 1.0065 even though no corrosion had occurred. Such a ratio is equivalent to a corrosion depletion of 0.129 mils, which is the corrosion occurring over a 4.7 day period in an environment causing an average rate of 10 mils corrosion per year. To compensate for this error, differential temperature between terminal C and D is measured by the iron-Constantan junctions at the connections of the C and D leads to the test and reference elements. For this 1° difference, which may be termed a compensation variable, the thermocouple junction causes a 55 microvolt differential voltage between terminals C and D. After amplification, after sensitivity scaling by means of adjustment potentiometer 94, and after digital conversion and digital averaging, the number 0.0065, which represents the measured 1° centigrade differential temperature, is fed to the corrosion depletion computing circuit. This number is added to unity by the computing circuit to give the desired 1.0065, which is termed the compensation factor. This compensation factor is divided in corrosion depletion computer 102 by the measured 1.0065 resistance ratio, resulting in a quotient of 1.0000, which indicates an absence of corrosion depletion. Thus, both primary and secondary compensation are accomplished. The mathematical calculations carried out in the corrosion depletion computer are specifically delineated in the system operation equation set forth below. It will be seen from this equation that the corrsison signal, namely a quantity representing the remaining thickness of the tubular test element, is multiplied by the compensation factor.

This method of combining the compensation signal with the corrosion signal accounts for the fact that the effect of the differential temperature (or other variable) changes as the test element corrodes, and, furthermore, is a function of the temperature coefficient of resistance. The simple algebraic combination of compensation and corrosion signals, as described in U.S. Pat. No. 4,338,563, for example, is accurate for one given condition of the test element (new condition, for example). But such method of combining the compensation signal is subject to error that varies as the test element continues to be depleted.

According to one feature of the present invention, compensation is achieved by multiplying the corrosion signal by the compensation signal. As can be seen in the equations set forth below, in one form of the corrosion signal the measured resistance ratio is in the denominator of the fractional quantity that represents the corrosion signal. This quantity is multiplied by the compensation factor, thereby achieving the quotient described above. As mentioned above, it has been found that the secondary temperature compensation also is a function of the temperature coefficient of resistance of the test element material. Therefore the compensation factor is calculated as the sum of unity and the product of the temperature differential and the temperature coefficient of resistance.

In order to understand the basis for the compensation equations set forth below, a reference temperature, $t_R$ is defined as the existing temperature of the reference element. For small changes in temperature of the test element from such a reference, the resistivity of the test element $\rho_T$ varies as follows:

$$\rho_T = \rho_R(1 + \alpha(t_T - t_R)) \qquad \text{Eq.(1)}$$

where $\rho_T$ is resistivity of the metal of the reference element at the reference temperature $t_R$, $\alpha$ is the temperature coefficient of resistance of the metal and $t_T$ is the temperature of the test element.

For a known probe configuration, $$\frac{R_T}{R_R} = \frac{\rho_T \frac{l_T}{A_T}}{\rho_R \frac{l_R}{A_R}} \qquad \text{Eq.(2)}$$

where $R_T$ and $R_R$ are the measured resistance of test and reference elements, respectively, $l_T$ and $l_R$ are lengths of the respective test and reference elements, and $A_T$ and $A_R$ are their respective cross sectional areas.

Therefore, when there is a difference of temperature, $\Delta T$, between the test and reference elements, where $\Delta T$ equals $t_T - t_R$, the ratio of resistances is $$\frac{R_T}{R_R} = \frac{l_T A_R \rho_R (1 + \alpha \Delta T)}{l_R A_T \rho_R} \qquad \text{Eq.(3)}$$

where the terms $\rho_R$ cancel from numerator and denominator. Equation (3) expresses the error factor equal to $1 + \alpha \Delta T$ in the measured resistance ratio, as caused by the difference in temperature between test and reference elements. Therefore if we measure $\Delta T$ and, at least to a close approximation, know the temperature coefficient of resistance $\alpha$, the ratio $R_T/R_R$ may be divided by a compensation factor $(1 + \alpha \Delta T)$ to cancel the resistance ratio error caused by $\Delta T$. In effect, if one simply divides the ratio $R_T/R_R$ by the compensation factor $1 + \alpha \Delta T$, compensation is provided for the difference in temperature between the elements.

In the equations expressing metal depletion for several different types of probes, there is a term in which the ratio $R_T/R_R$ is in the denominator of a fraction. Thus for a tubular probe, the depletion d is expressed as follows:

$$d = K_1 - \frac{K_2}{\frac{R_T}{R_R}} \qquad \text{Eq.(4)}$$

For a thin tubing or strip probe, depletion is expressed as follows:

$$d = K_3 - \frac{K_4}{\frac{R_T}{R_R} - K_5} \qquad \text{Eq.(5)}$$

and for a wire loop probe, depletion is as follows:

$$d = K_6 - \frac{K_7}{\frac{R_T}{R_R} + K_8} \qquad \text{Eq.(6)}$$

where d is the corrosion depletion of the exposed test element and $K_1$ through $K_8$ are constants. Therefore, with the ratio $R_T/R_R$ in each of Equations (4), (5) and (6), division of the ratio by the compensation factor $1 + \alpha \Delta T$ is achieved by dividing $R_T/R_R$ by the compensation factor $1 + \alpha \Delta T$. This division is achieved in Equation (4) by multiplying the quantity $K_2/R_T/R_R$ by the factor $1 + \alpha \Delta T$ and in each of Equations (5) and (6) by dividing the ratio $R_T/R_R$ by such factor.

The above reasoning also applies to other compensations to be described below such as caused, for example, by the pressure variable, the velocity or strain variable, and the temperature gradient variable. The operations for multiplying the corrosion quantity by the appropriate compensation factor, are all delineated in the complete system equation set forth below in Equation (7).

Even after having performed both primary and secondary compensation, there remains still another source of correlated noise caused by temperature. This noise source is the temperature gradient along the test and reference elements. In the case of a tubular corrosion probe, the temperature gradient is most prevalent along the corrosion protected reference element. This is so because the physical arrangement of materials and configuration that is required to protect the reference element from the corrosive environment inherently isolates the reference element and insulates it to some degree from the temperature of the environment into which the probe is inserted.

As can be seen in the probe configurations illustrated in both FIGS. 1 and 3, the inner end of the reference element is at or within the corrosive environment, though not in contact therewith, while the outer end of the reference element is more thermally insulated from the environment. The thermocouple junctions at terminals C and D, detect temperatures of the test and reference elements only at a single point, each, for the purpose of the secondary temperature compensation. Such sensed points have been assumed to be representative of the effective temperatures of the respective elements for secondary temperature compensation. Nevertheless, if there is a temperature differential between the inboard and outboard ends of the probe, there is a significant temperature gradient, especially along the reference element. Therefore the point at which the terminal D is connected to the reference element may not be representative of the effective reference element temperature. It has been found that temperature gradients along the test and reference elements are nearly a linear function of the differential between environment temperature (inboard temperature) and the temperature at the outside of the vessel (outboard temperature) adjacent the probe. Because of complexity of probe structure, it is difficult, if not impossible, to determine a proportionality coefficient by analytical means. Therefore the coefficient of the thermal gradient compensation is established empirically for each probe type. It may be noted that the temperature gradient coefficient established for a probe using secondary temperature compensation is not the same as the temperature gradient coefficient established for a probe that does not employ secondary temperature compensation.

Figures 5, 6:
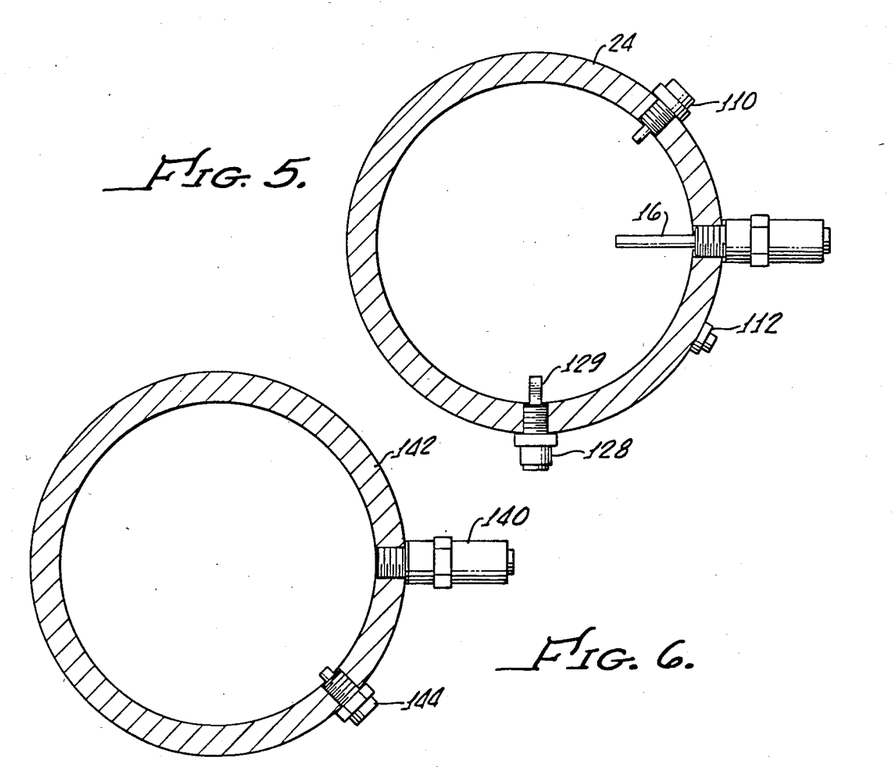
FIG. 5 is a sectional view of a pipe showing a typical corrosion probe and rtransducer relation.
FIG. 6 is a sectional view of a pipe having a flush mounted probe and pressure tranducer.

To accomplish temperature gradient compensation, a fluid temperature transducer 110 (FIG. 5) is mounted in the vessel 24 adjacent the probe body 16 for measuring temperature of the fluid environment adjacent the probe. A second temperature transducer 112 is mounted to the vessel wall 24 adjacent the probe but positioned and configured to measure temperature at the outboard end of the probe, outside of the vessel. Conveniently, the transducers 110 and 112 may be thermocouples.

As illustrated in FIG. 4, signals from thermocouples 110, 112 are fed to temperature circuits 114, 116, respectively, to provide fluid temperature signal $T_F$ and external vessel temperature signal $T_V$ to a differential amplifier 118 of which the output is fed to a thermal gradient sensitivity compensation adjusting potentiometer 120. The differential temperature signal (the difference between temperatures measured at thermocouples 110 and 112), as adjusted by potentiometer 120, is converted to a digital value in an analog-to-digital converter 122 of which the output is fed to a digital averaging circuit 124 that performs a digital averaging of a type described above in connection with circuits 82,84,98. Thus, the output of averaging circuit 124 on a line 126 is a temperature gradient compensation signal that is fed to the corrosion depletion computing circuit 102 and combined with the ratio on line 88 in the same manner as the secondary temperature compensation signal. The compensation signal on line 126 is a compensation variable that is added to unity to provide the thermal gradient compensation factor. This compensation factor is then divided by the number representing the measured resistance ratio, as provided on line 88. It is found that even where the secondary temperature compensation is employed, the use of the additional temperature gradient compensation provides still further improvement in accuracy of the output signal and a decrease in errors due to temperature.

Adjustment of compensation sensitivity potentiometer 120 is determined empirically for each probe type. The probe is inserted into a typical vessel, such as a pipe, with the two gradient temperature tranducers installed as described above. A low corrosivity liquid, such as distilled water, is caused to flow at a slow rate past the probe and past the internal temperature transducer, with the liquid held at room temperature so that virtually no differential temperature exists. After temperature equilibrium is established, that is, after the measured depletion output on line 156 is stabilized, the measured depletion value is recorded. Temperature of the flowing liquid is then increased to about 20° centigrade above room temperature and the temperature differential allowed to stabilize for several hours. After stabilization, the potentiometer is adjusted slowly until the depletion output reading stabilizes at the same value as the value recorded initially. The potentiometer setting to achieve this last-mentioned stabilization is noted and such a setting is used for all systems having the type of probe tested. The reading stabilization time must occur over at least several data averaging periods to minimize errors due to uncorrelated noise.

Flow of fluid through a pipe or other vessel that mounts a probe of the elongated type, such as a thin wall tubular or loop type probe, tends to bend a portion of the probe that projects into the flowing fluid stream. The bending stress thus created changes electrical resistance of the test element. It is found that stress on the probe elements, and particularly on the exposed test element, is primarily caused by velocity of fluid flowing in a direction perpendicular to the axis of the probe. Stress is found to be nearly proportional to the square of such velocity. It has been found that a strain gauge mounted on a thin cantilevered metal vane that is installed adjacent to the probe and which extends along an axis perpendicular to fluid flow velocity, provides a strain measurement that is directly proportional to the strain on the probe caused by the fluid flow. A compensating proportionality constant for combining the strain gauge signal and resistance ratio signal is empirically determined for each probe type. For fluid flow velocity, or more particularly for measurement of strain due to flow velocity, a strain gauge 128 (FIG. 5) is mounted in the wall of vessel 24 adjacent the probe. The gauge 128 includes a resilient flat blade 129 having a strain measuring element thereon. The blade is cantilevered to extend into the environment in a direction perpendicular to the direction of fluid flow. Blade 129 is subjected to a bending stress due to fluid flow. The stress and resulting strain are measured by strain gauge 128 to provide a strain signal to a strain gauge circuit 130 (FIG. 4). The analog output of the strain gauge circuit 130 is multiplied by a proportionality constant in an adjustable potentiometer 132 of which the output is digitized in an analog-to-digital converter 134. The resulting digital signal is averaged in a digital averaging circuit 136 in a manner similar to that previously described to provide an averaged digital strain compensation signal on a lead 138 which is also fed to the corrosion depletion computing circuit 102, where it is combined with the ratio signal is the same manner as the other compensation signals are combined therewith.

As described above, an additional environment parameter that will provide a strain on a transducer, particularly a transducer of the flush type, is fluid pressure. Thus, where a flush type probe 140 (FIG. 6) is mounted in the wall of a pipe or other vessel 142, a pressure transducer 144 is also mounted in the pipe wall adajcent the probe to provide an output electrical signal indicative of pressure of the fluid within the pipe.

As illustrated in FIG. 4, the pressure signal from transducer 144 is fed to gauge pressure circuit 146, and thence fed as the signal P through a compensation adjusting potentiometer 148 to an analog-to-digital converter 150 of which the digital output is averaged in a digital averaging circuit 152. The latter provides on its output lead 154 a fluid pressure compensating signal that is also fed to the corrosion depletion computer for compensation of the ratio signal in the manner described above in connection with the other compensation signals.

The fully compensated corrosion depletion signal is provided from computing circuit 102 on an output lead 156, providing a corrosion reading in mils. The corrosion output signal may also be fed to a corrosion rate computer 158 that provides an output signal on a lead 160 representing the rate of corrosion, which may be measured in mils per year.

To empirically determine the potentiometer adjustment for each of the strain gauge and pressure gauge, a procedure similar to that described for temperature gradient potentiometer adjustment is followed. The potentiometer adjustment is determined for zero flow velocity, or zero pressure, to establish a constant depletion reference value. Then a constant high velocity or high pressure, respectively, is provided while potentiometer adjustment is made to compensate for the effects of the higher velocity or pressure, and to bring the output depletion back to its reference value.

Any one or more of the described compensation factors may be employed for maximum compensation of output of any probe. Where several of the described factors are employed, the compensation variables, after being added to unity to provide the respective compensation factors, are multiplied by each other with the resulting product divided by the measured resistance ratio, as set forth in the following equation.

The equation defining the operation of the corrosion depletion computer and operation of the system, when using all of the above described compensation methods with a thin wall tubular type probe, is as follows:

$$d = t_{TN} - t_{TN}\left[\frac{\left[\frac{R_T}{R_R}\right]_N}{\frac{R_T}{R_R}}\right](1 + \alpha\Delta T)(1 + K_T(T_F - T_V))(1 + K_S S)(1 + K_P P) \quad \text{Eq.(7)}$$

where:
- d = corrosion depletion (mils),
- $t_{TN}$ = test wall thickness when new (mils),
- $[R_T/R_R]_N$ = ratio of test element resistance to reference element resistance, when new,
- $\alpha$ = temperature coefficient of resistance for the probe metal type (°C.$^{-1}$),
- $\Delta T$ = measured differential temperature between the two thermocouple junctions (°C.),
- $R_T/R_R$ = resistance ratio measured during test,
- $(T_F - T_V)$ = differential temperature measured between the fluid and the external side of the vessel wall,
- $K_T$ = emperically determined coefficient for temperature gradient compensation,
- S = measured strain,
- $K_S$ = emperically determined coefficient for strain compensation,
- P = measured pressure,
- $K_P$ = emperically determined coefficient for pressure compensation.

In the above equation, it will be seen that each compensation variable, such as $\alpha\Delta T$ for secondary temperature and $K_S S$ for strain, is added to unity and the resulting sum is divided by the measured resistance ratio that forms part of the corrosion signal used in calculating corrosion depletion. Calculation of the measured resistance ratio is performed in the ratio computer 86. The remaining calculations of the system equation are carried out in computer 102.

If any one of the above-described compensations is omitted, the compensation factor in the above equation becomes unity and has no effect on the computation. Thus for a probe of any given type, one may employ any one or any combination of secondary temperature compensation, temperature gradient compensation, strain compensation for flow velocity and strain compensation for pressure.

The described method of combining one or more of the compensation factors with the corrosion signal is applicable to probes of many different configurations, such as solid circular or rectangular section wire probes, ribbon probes, and the like. For probes of other than tubular shape, such as a solid circular cross section wire probe, for example, the quantity defining the corrosion signal (e.g. that protion of the above equation to the left of the several compensation factors) will be different (see Equation (6) above). Nevertheless the compensation factors will still be multiplied by each other and the resulting product divided by the measured ratio, $R_T/R_R$.

The temperature coefficient of resistance, $\alpha$, for various metals is a known non-linear function of temperature, which, for example, in iron decreases slightly with a rise in temperature at lower temperatures, and then increases slightly with further increase in temperature. When using temperature gradient compensation, a signal representing the approximate temperature of the probe is available from the fluid temperature circuit, 114. Thus the secondary temperature compensation signal, which is a function of $\alpha\Delta T$ may use a temperature coefficient $\alpha$ that is corrected for temperature. To accomplish such correction, it is only necessary to digitize the output $T_F$ from circuit 114 and use this digitized signal in the corrosion depletion computer to correct the temperature coefficient $\alpha$ employed for the secondary temperature compensation.

There have been described methods and apparatus for maximizing compensation of an electrical resistance probe for environmental factors that are correlated with the probe output signal and for minimizing errors due to uncorrelated noise, thereby to achieve a probe capable of increased precision of short period corrosion measurement.

The foregoing detailed description is to be clearly understood as given by way of illustration and example only, the spirit and scope of this invention being limited solely by the appended claims.

What is claimed is:

1. In an electrical resistance-type corrosion measurement system, having test and reference elements mounted in a probe adapted to be placed in a fluid environment of which corrosive characteristics are to be measured, and having means for providing a corrosion signal representing corrosion of said test element, said signal having a compensation for temperature of said environment, the improvement comprising apparatus for further compensating said signal for fluctuation of an environment variable that affects said corrosion signal, said variable comprising the temperature gradient between said environment and a point adjacent the probe outside said environment, said apparatus comprising means responsive to said environment variable for measuring said variable and generating an auxiliary compensation signal representing the value of such variable, and means for combining the corrosion signal with said auxiliary compensation signal to provide an output signal representative of corrosion of said test element compensated for variation of said variable.

2. The system of claim 1, wherein said auxiliary compensation signal is a temperature gradient compensation signal, and wherein said apparatus for compensating comprises first temperature measuring means for measuring temperature of said fluid environment adjacent said probe, second temperature measuring means for measuring temperature of said probe at a point external to said fluid environment, and means for comparing temperatures measured by said first and second temperature measuring means to generate said temperature gradient compensation signal, said means for combining said corrosion signal comprising means for combining said temperature gradient compensation signal with said corrosion signal.

3. The system of claim 1, wherein said means for providing a corrosion signal comprises means for computing the ratio of measured resistance of said test and reference elements, and wherein said means for combining comprises computing the ratio of (a) the sum of unity and said auxiliary compensation signal to (b) said ratio of measured resistances.

4. The system of claim 1 including means responsive to a second environment variable for generating a second auxiliary compensation signal representing the value of a second environment variable, said second environment variable comprising flow velocity of said environment, said means for combining including means for combining both said auxiliary compensation signals with said corrosion signal to provide an output signal representative of corrosion of said test element compensated for variation of a plurality of environment variables.

5. The corrosion system of claim 4 wherein said means for providing a corrosion signal includes means for measuring resistances of said test and reference elements and computing the ratio of the measured resistances, and wherein said means for combining comprises computing the ratio of (a) the product of first and second auxiliary compensation factors and (b) said corrosion signal, each said factor comprising the sum of unity and a respective one of said auxiliary compensation signals.

6. The corrosion system of claim 1 wherein said means for generating at least one of said corrosion and auxiliary compensation signals comprises means for generating a measured signal representative of a measured quantity and means for averaging values of the measured signal over a selected period.

7. In an electrical resistance-type corrosion measuring system, having test and reference elements mounted in a probe adapted to be placed in a fluid environment of which corrosive characteristics are to be measured, and having means for providing a corrosion signal representing corrosion of said test element, said signal having a compensation for temperature of said environment, the improvement comprising apparatus for further compensating said signal for fluctuation of an environment variable that affects said corrosion signal, said variable comprising pressure of fluid of said environment, said apparatus comprising means responsive to said environment variable for measuring said variable and generating an auxiliary compensation signal representing the value of such variable, and means for combining the corrosion signal with said auxiliary compensation signal to provide an output signal representative of corrosion of said test element compensated for variation of said variable.

8. The system of claim 7, wherein said auxiliary compensation signal is a pressure compensation signal, and wherein said means for measuring said variable comprises means for measuring pressure of said environment to generate said pressure compensation signal, whereby combining said corrosion signal with said pressure compensation signal will provide an output signal representative of corrosion of said test element compensated for said pressure of said fluid environment.

9. The method of providing compensation of a corrosion probe of the type having a test element arranged for exposure to a corrosive fluid environment within a vessel, a reference element protected from the environment, and means for measuring electrical resistance of the reference and test elements to obtain a corrosion signal indicative of corrosion of the test element, said corrosion signal being affected by one of the variables of said fluid environment, said one variable comprising temperature gradient between said fluid environment and a point adjacent the probe external to said vessel, said method comprising sensing said one variable to generate a variable compensation signal representative of said one variable, and employing said variable compensation signal to compensate the corrosion signal.

10. The method of claim 9 wherein said step of sensing comprises sensing temperature of said probe within said fluid environment, sensing temperature of the probe external to said fluid environment, and generating a temperature gradient compensation signal representing a predetermined relation between the sensed temperatures, whereby said temperature gradient compensation signal may be combined with said corrosion signal for compensation thereof.

11. The method of providing compensation of a corrosion probe of the type having a test element arranged for exposure to a corrosive fluid environment within a vessel, a reference element protected from the environment, and means for measuring electrical resistance of the reference and test elements to obtain a corrosion signal indicative of corrosion of the test element, said corrosion signal being affected by one of the variables of said fluid environment, said one variable comprising pressure of said fluid environment adjacent said probe, said method comprising sensing said one variable to generate a variable compensation signal representative of said one variable, and employing said variable signal to compensate the corrosion signal.

12. The method of claim 11 wherein said step of sensing comprises sensing pressure within the fluid environment adjacent said probe to generate a pressure compensating signal representing said pressure, whereby said pressure compensating signal may be combined with said corrosion signal to provide pressure compensation therefor.

13. The method of claim 9 wherein said corrosion signal is obtained from the ratio of measured resistances of said test and reference elements, and wherein said step of employing said variable signal to compensate said corrosion signal comprises computing the ratio of (a) the sum of unity and said variable signal to (b) said ratio of measured resistances.

14. A corrosion measuring system comprising a test element adapted to be exposed to an environment of which corrosive characteristics are to be measured, a reference element mounted adjacent said test element and protected from corrosion by said environment, means for generating a corrosion signal having a first compensation for temperature of said elements, means responsive to the difference in temperature between said test and reference elements for generating a secondary temperature compensation signal representative of the difference in temperature between said test and reference elements, means responsive to the temperature gradient between a point within said environment and a point outside of said environment for generating a temperature gradient compensation signal, and means for combining both said compensation signals with said corrosion signal to provide a compensated corrosion signal.

15. The corrosion system of claim 14 wherein said means for generating a temperature gradient compensation signal comprises means for sensing first and second temperatures at points respectively within and outside of said environment adjacent said test element, and means for generating said temperature gradient compensation signal as a predetermined function of both said first and second temperatures.

16. The corrosion system of claim 14 wherein said means for generating a corrosion signal comprises means for computing the ratio of measured resistances of said test and reference elements, wherein said means for generating a secondary temperature compensation signal comprises means for computing a first sum of unity and a quantity representing the difference in temperature between said test and reference elements, wherein said means for generating a temperature gradient compensation signal comprises means for computing a second sum of unity and a quantity representing the difference in temperature between points adjacent said test element respectively within and outside of said environment, and wherein said means for combining comprises computing the ratio of (a) the product of said first and second sums and (b) said corrosion signal.

17. The corrosion system of claim 14 wherein said means responsive to the difference in temperature includes means for measuring temperature of said test and reference elements, wherein said secondary temperature compensation signal is generated as a function of $\alpha \Delta T$, where $\alpha$ is the temperature coefficient of resistance of said test element and $\Delta T$ is the difference in measured temperatures of said test and reference elements, and including means responsive to measured temperature of one of said elements for compensating said temperature coefficient of resistance for variation in temperatures.

18. For use with a vessel having a wall that confines a fluid environment of which corrosive characteristics are to be measured, improved electrical resistance corrosion probe apparatus comprising a probe body extending through said wall and including a test element extending into said fluid environment for exposure thereto, a reference element mounted adjacent said test element and protected from the corrosion by said environment, resistance responsive means for generating a corrosion signal having a first compensation for temperature of said elements, a transducer mounted in said vessel adjacent said probe for measuring flow velocity of fluid adjacent said probe, means responsive to said transducer for generating a strain compensation signal representative of strain of said test element due to flow velocity of fluid within said vessel, and means for combining said strain compensation signal with said corrosion signal to provide compensation for effects of fluid flow velocity on said corrosion signals.

19. The apparatus of claim 18 wherein said transducer comprises a test blade extending into said fluid environment across the direction of fluid flow, and means for measuring strain on said blade resulting from flow of fluid against the blade.

20. In combination with a vessel including a wall that confines a fluid environment of which corrosive characteristics are to be measured, an improved electrical resistance corrosion probe comprising a probe body extending through said wall and including a test element in contact with said fluid environment for exposure thereto, a reference element mounted adjacent said test element and protected from corrosion by said environment, resistance responsive means for generating a corrosion signal having a first compensation for temperature of said elements, a pressure transducer mounted in said vessel adjacent said probe for measuring pressure of fluid adjacent said probe, means responsive to said pressure transducer for generating a pressure compensation signal representative of pressure of fluid within said vessel, and means for combining said pressure compensation signal with said corrosion signal to provide compensation for effects of pressure on said corrosion signal.

21. The combination of claim 20 wherein said electrical resistance probe is a flush probe having a thin metallic plate extending in a plane generally parallel to and flush with said vessel wall.

22. An electrical resistance-type corrosion measuring system, comprising test and reference elements mounted in a probe adapted to be placed in a fluid environment of which corrosive characteristics are to be measured, means for measuring resistances of said test and reference elements, ratio means responsive to said measuring means for providing a corrosion signal representing corrosion of said test element compensated for temperature of said enviroment, said ratio means comprising means for computing the ratio of measured resistance of said test and reference elements, apparatus for further compensating said corrosion signal for fluctuation of an environment variable that affects said corrosion signal, said apparatus comprising means responsive to said environment variable for generating a compensation variable, means for computing the sum of unity and said compensation variable, and means for multiplying said corrosion signal and said sum to provide an output signal representative of corrosion of said test element compensated for said environment variable.

23. The system of claim 22 wherein said compensation variable is a temperature gradient compensation variable and wherein said means for generating a compensation variable comprises first temperature measuring means for measuring temperature of said fluid environment adjacent said probe, second temperature measuring means for measuring temperature of said probe at a point external to said fluid environment, and means for comparing temperatures measured by said first and second temperature measuring means to generate said temperature gradient compensation variable.

24. The system of claim 22 wherein said compensation variable is a velocity compensation variable, and wherein said means for generating a compensation variable comprises means for measuring velocity of flow of fluid of said environment.

25. The system of claim 22 wherein said compensation variable is a pressure compensation variable, and wherein said means for generating a compensation variable comprises means for measuring pressure of said environment.

26. The system of claim 22 wherein said compensation variable is a secondary temperature compensation variable, and wherein said means for generating a compensation variable comprises temperature means for measuring the temperature differential between said test and reference elements, and means responsive to said temperature means for generating said secondary temperature compensation variable.

27. The system of claim 22 wherein said environment variable is relatively short term temperature variation, wherein said means for generating a compensation variable comprises means for measuring temeperature differential between said test and reference elements, said means for computing comprising means for adding unit to the product of said measured temperature differential and the temperature coefficient of resistance of said test element.

28. A corrosion measuring instrument comprising
a test element adapted to be exposed to an environment of which corrosive characteristics are to be measured,
a reference element mounted adjacent said test element and protected from corrosion by said environment,
means for generating a corrosion signal having a first compensation for temperature of said elements, said means comprising means for computing the ratio of measured resistances of said test and reference elements,
means responsive to the difference in temperature between said test and reference elements for generating a secondary temperature compensation signal representative of the difference in temperature between said test and reference elements, and
means for combining said secondary temperature compensation with said corrosion signal to provide a compensated corrosion signal, said means for combining comprising
means for computing the sum of unity and said secondary temperature compensation signal, and
means for computing the product of said sum and said corrosion signal.

29. The system of claim 28 wherein said secondary temperature compensation signal represents a quantity including the product of said temperature difference and the temperature coefficient of resistance of said test element, said means for computing the product of said corrosion signal and said secondary temperature compensation signal comprising means for computing the ratio of said quantity to the ratio of said measured resistances.

30. In an electrical resistance-type corrosion measuring system, having test and reference elements mounted in a probe adapted to be placed in a fluid environment of which corrosive characteristics are to be measured, and having means for providing a corrosion signal representing corrosion of said test element, said signal having a compensation for temperature of said environment, the improvement comprising apparatus for further compensating said signal for fluctuation of an environment variable that affects said corrosion signal, said variable comprising velocity of fluid flowing in said environment, said apparatus comprising
means responsive to said environment variable for measuring said variable and generating an auxiliary compensation signal representing the value of such variable, and
means for combining the corrosion signal with said auxiliary compensation signal to provide an output signal representative of corrosion of said test element compensated for variation of said variable.

31. The system of claim 30, wherein said auxiliary compensation signal is a velocity compensation signal, and wherein said means for measuring said variable comprises means for measuring velocity of flow of fluid of said environment to generate said velocity compensation signal, whereby combining said velocity compensation signal with said corrosion signal will provide an output signal representative of the corrosion of the test element compensated for flow velocity of the fluid environment.

32. The method of providing compensation of a corrosion probe of the type having a test element arranged for exposure to a corrosive fluid environment within a vessel, a reference element protected from the environment, and means for measuring electrical resistance of the reference and test elements to obtain a corrosion signal indicative of corrosion of the test element, said corrosion signal being affected by one of the variables of said fluid environment, said one variable comprising velocity of said fluid environment adjacent said probe, said method comprising
sensing said one variable to generate a variable compensation signal representative of said one variable, and
employing said variable compensation signal to compensate the corrosion signal.

33. The method of claim 32 wherein said step of sensing comprises sensing velocity of fluid of said environment to generate a velocity signal representing said velocity, whereby said velocity signal may be combined with said corrosion signal to provide velocity compensation therefore.

* * * * *

UNITED STATES PATENT AND TRADEMARK OFFICE
CERTIFICATE OF CORRECTION

PATENT NO.   :   4,587,479

DATED        :   May 6, 1986

INVENTOR(S)  :   Rex V. Rhoades et al.

It is certified that error appears in the above-identified patent and that said Letters Patent is hereby corrected as shown below:

Claim 1 (column 12, lines 1 and 2), delete "measurement" and substitute therefor ---measuring---.

Claim 27 (column 17, line 30), delete "unit" and substitute therefor ---unity---.

Signed and Sealed this

Seventh Day of April, 1987

Attest:

DONALD J. QUIGG

Attesting Officer

Commissioner of Patents and Trademarks